United States Patent [19]

Cage et al.

[11] Patent Number: 5,861,316
[45] Date of Patent: Jan. 19, 1999

[54] CONTINUOUS EMISSION MONITORING SYSTEM

[75] Inventors: Brian R. Cage, Shawnee; Paul G. Gorman, Prairie Village, both of Kans.; John E. Going, Kansas City, Mo.; Michael J. Thornburg, Overland Park, Kans.; Daniel R. Soderberg, Kansas City, Mo.

[73] Assignee: Midwest Research Institute, Kansas City, Mo.

[21] Appl. No.: 697,137

[22] Filed: Aug. 20, 1996

Related U.S. Application Data

[63] Continuation of Ser. No. 329,149, Oct. 25, 1994, abandoned.

[51] Int. Cl.$^6$ .................................................. B01D 47/00
[52] U.S. Cl. .................. 436/52; 73/23.12; 73/863.12; 436/83; 436/174; 436/177; 436/181; 422/82.01; 422/82.03; 422/88; 422/90; 55/235; 55/236; 55/237; 55/238; 55/210; 96/101; 96/181; 96/209; 96/216; 96/197; 95/82; 95/219
[58] Field of Search .............................. 436/52, 83, 174, 436/177, 181; 427/80.01, 90, 82.03, 88; 55/235, 236, 237, 238, 270; 96/181, 209, 216, 197, 101; 95/82, 219; 73/863.12, 23.12

[56] References Cited

U.S. PATENT DOCUMENTS

| | | | |
|---|---|---|---|
| 3,044,236 | 7/1962 | Baerden et al. | 55/270 |
| 3,581,469 | 6/1971 | Davis | 73/863.12 |
| 3,960,523 | 6/1976 | Ryan | 55/84 |
| 3,976,450 | 8/1976 | Marcote et al. | 55/158 |
| 3,990,870 | 11/1976 | Miczek | 55/236 |
| 4,014,787 | 3/1977 | Shorr | 210/23 F |
| 4,117,714 | 10/1978 | Goodson et al. | 73/23 |
| 4,479,379 | 10/1984 | Tarcy | 73/23 |
| 5,011,517 | 4/1991 | Cage et al. | 55/92 |
| 5,132,094 | 7/1992 | Godec et al. | 422/68.1 |
| 5,451,318 | 9/1995 | Moorehead | 210/512.1 |
| 5,514,279 | 5/1996 | Blowes et al. | 210/617 |
| 5,679,580 | 10/1997 | Ball et al. | 436/177 |

FOREIGN PATENT DOCUMENTS

| 1613949A | 2/1988 | U.S.S.R. | 436/52 |
|---|---|---|---|

OTHER PUBLICATIONS

Going et al "Prototype Near Real–Time Monitor for Lewisike in Stack Gas" Therm. Treat. Radioact. Hazard. Chem. Mixed Mumitions, Pharm. Wastes Proc. Int. Incineration Conf. 13th (1994) 569–573.

Kneetzone et al "Determination of Chromium (VI) in Industrial Atmospheres by a Catalytic Method" Analyt. Chem. vol. 47, #3 Mar. 1975, pp. 595–598.

Bossle, et al. Determination of 2–Chlorovinyl arsonic Acid in Environmental Waters by Ion Chromatography. Chemical Research Development & Engineering Center, AD–A226769, Sep. 1990.

*Primary Examiner*—Harold Y. Pyon
*Assistant Examiner*—Sharidan Carrillo
*Attorney, Agent, or Firm*—Chase & Yakimo, L.C.

[57] ABSTRACT

A continuous emission monitoring system is disclosed for detecting toxic substances of various types in either stack gas or ambient air. Particular systems are illustrated for monitoring lewisite and chromium(VI). Each system employs a gas sampler that utilizes a high-volume, wet cyclone concentrator unit which scrubs the contaminants from the gas into water or another suitable scrubbing solution. In-line chemical processing of the contaminated sample thus obtained is accomplished either within the sampling unit or by an external chemistry processing module. After processing to provide an analyte in the sample indicative of the presence of a predetermined contaminant, the sample stream is delivered to an ion chromatograph or other analyzer to determine the presence and quantity of the analyte and indicate whether a danger level has been reached. This provides monitoring on an essentially real-time or near real-time basis.

15 Claims, 5 Drawing Sheets fig. 1

Fig. 4 fig. 6

CONTINUOUS EMISSION MONITORING SYSTEM

This application is a continuation of application Ser. No. 08/329,149, filed Oct. 25, 1994, now abandoned.

BACKGROUND OF THE INVENTION

This invention relates to improvements in systems for monitoring harmful emissions that may be present in stack gas or ambient air and, in particular, to an improved system which provides monitoring on a near real-time basis and which employs a wet cyclone concentrator in conjunction with appropriate in-line chemical processing to provide a processed sample that may be immediately analyzed for the presence of a predetermined contaminant.

Existing methods for analysis of toxic contaminants in stack gas and in the workplace typically require the collection of air or gas samples through bubblers for an extended period of time. Analysis of the contaminated samples is conducted in a laboratory. The time thus required for collection and analysis can be a dangerous delay when particularly hazardous substances may be present as either a stack gas emission or an air pollutant in the workplace.

Concentrators capable of extracting trace contaminants from air have been proposed and are disclosed in U.S. Pat. Nos. 4,117,714 and 5,011,517, owned by the assignee herein. The air or other gas swirls in the concentrator in intimate contact with a scrubbing liquid such as water and thus impurities in the air are extracted into the water which thereby becomes contaminated and may be withdrawn and analyzed. However, there is no assurance that the substances scrubbed from the air will be in a readily detectable form, or amenable to analysis on a near real-time basis by conventional analyzers.

Furthermore, the need for continuous emission monitors that will operate on a near real-time basis is increasing with the ever-growing governmental requirements for protection of the environment. Also, demilitarization of weapons stockpiles has added to the number of possible contaminants for which such monitoring systems must be adapted.

SUMMARY OF THE INVENTION

It is, therefore, an important object of the present invention to provide a continuous emission monitoring system which will operate on at least a near real-time basis and may be adapted to the detection of any of a number of contaminants that may be present in monitoring applications.

In furtherance of the foregoing object, it is an important aim of this invention to provide such a system in which a gas sampler employing a cyclone concentrator unit scrubs contaminants from a gas under observation, and in which the contaminated sample thus obtained is subjected to in-line chemical processing to provide a detectable substance therein indicative of the presence of a predetermined contaminant.

Another important object of the invention is to provide a system as aforesaid in which the detectable substance obtained through chemical processing may be immediately analyzed by conventional analyzers to determine the presence and quantity of the substance therein.

Still another important object is to provide such a system employing a gas conditioner ahead of the gas sampler in order to provide the gas under observation with a preselected temperature and moisture content prior to introduction to the sampler.

Yet another important object is to provide a continuous emission monitoring system which operates on at least a near real-time basis and provides in-line chemical processing of the sample to be analyzed, either during the sampling operation or thereafter in a chemistry processing module as may be appropriate for the specific analyte that is indicative of the presence of the target impurity.

Other important objects of the invention include the provision of continuous monitoring systems for lethal agents from chemical weapons, such as lewisite, and toxic metallic industrial impurities such as chromium(VI) and other metals in stack emissions.

Lewisite Monitor

Figure 1:
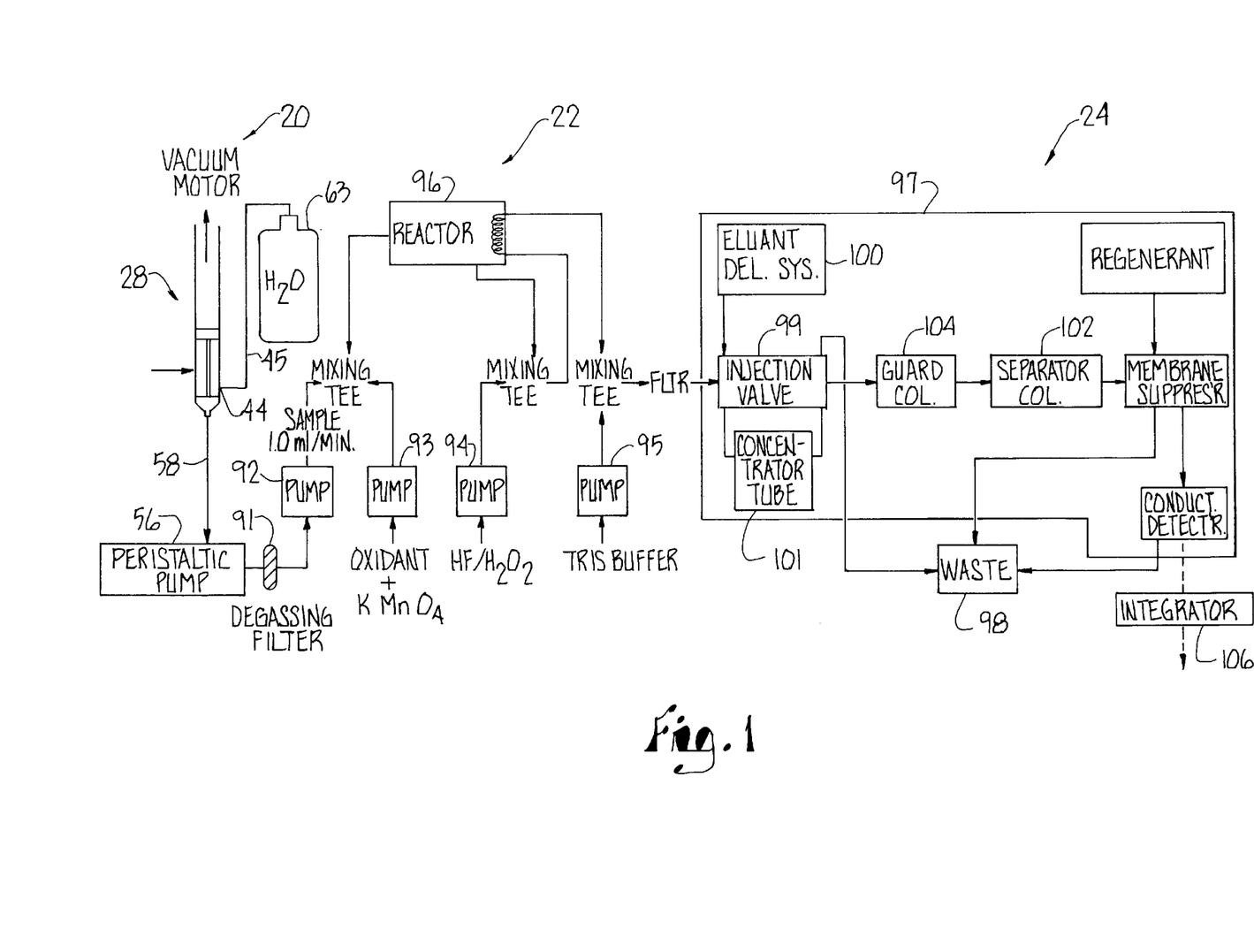
FIG. 1 is a block diagram of a monitoring system for use in the detection of lewisite emissions in stack gas or ambient air.

One application of the continuous emission monitoring system of the present invention illustrated herein is a near real-time monitor for lewisite emissions that may be present in either stack gas or ambient air at sites where chemical weapon stockpiles are undergoing demilitarization. Referring to FIG. 1, the subsystems of the monitor include a gas sampler 20, a chemistry processing module 22 and an ion chromatograph analysis system 24. In applications where stack gas is to be monitored, a gas conditioner 26 (FIG. 5) is employed ahead (upstream) of the sampler 20.

Figures 2, 3:
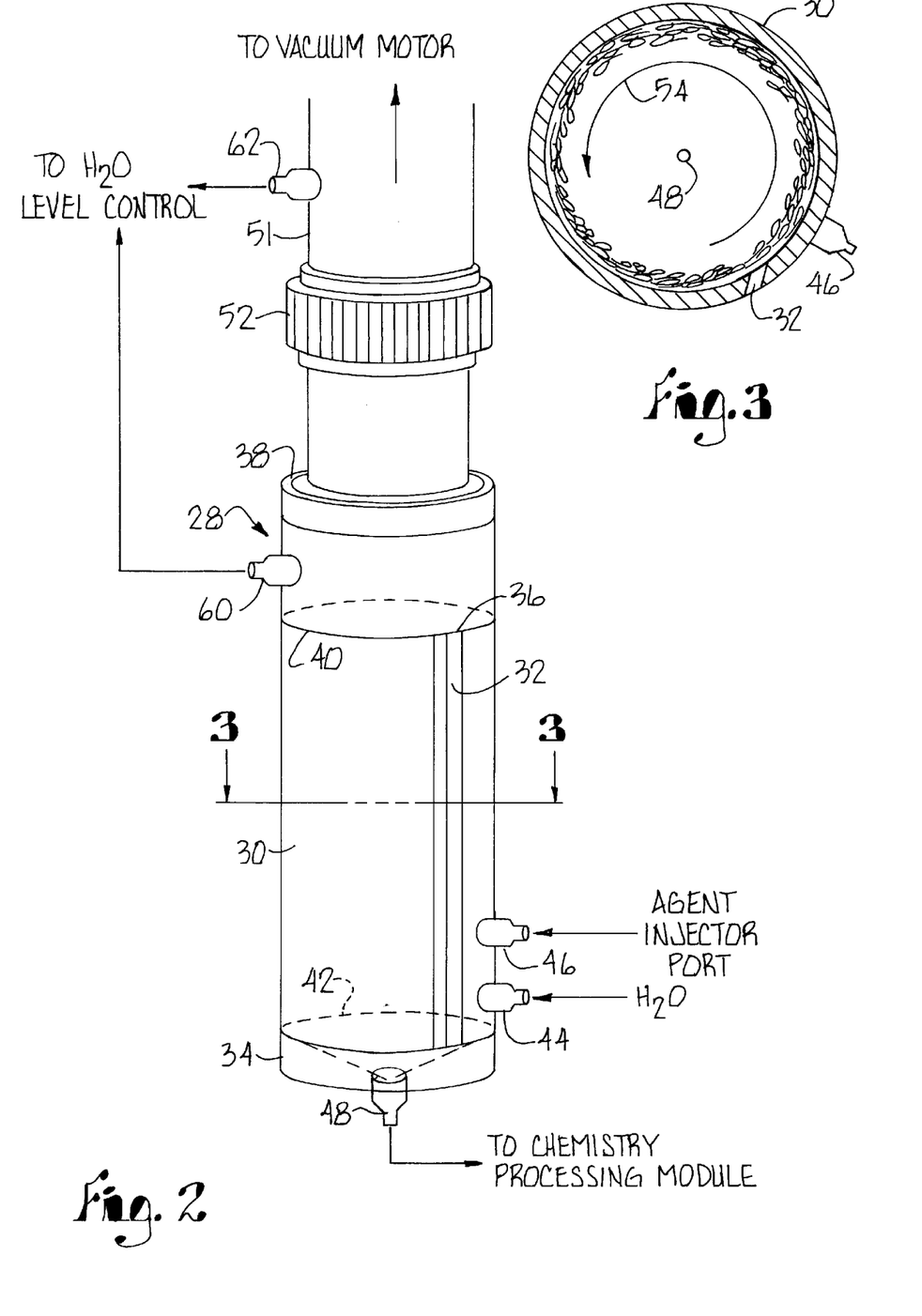
FIG. 2 is a perspective, diagrammatic view of a gas sampling unit utilized with the system of FIG. 1.
FIG. 3 is a horizontal cross-section through the cylindrical body of the sampling unit taken along line 3—3 of FIG. 2 and shows the swirling scrubbing liquid adjacent the interior wall surface, the arrows indicating gas flow into the inlet slit and within the cylindrical body.

The gas sampler 20 of the monitor employs a high-volume, wet cyclone concentrator unit of the general type disclosed in the aforesaid U.S. Pat. Nos. 4,117,714 and 5,011,517. The unit comprises an upright cylindrical receptacle 28 preferably made from clear acrylic plastic annealed to resist cracking during continuous exposure to a stack gas environment. The receptacle 28 presents a relatively thin, cylindrical wall 30 having an elongated, vertical inlet slit 32 therein extending from a circular, concave base plate 34 to a termination 36 spaced from the upper end 38 of the receptacle 28. The main body of receptacle 28 may, for example, be 4½ inches (11.4 cm.) in length and have an outside diameter of 2.0 inches (5.1 cm.) with a wall thickness of 0.125 inch (0.32 cm.). The slit 32 is cut the entire length of the main body, tangential to the wall 30, as shown in FIGS. 2 and 3 and may have a width of 0.05 to 0.2 inch (1.3 to 5.1 mm.). For clarity of illustration, the boundaries of the main body are denoted by circular upper and lower lines 40 and 42 on wall 30.

An inlet port 44 for scrubbing water communicates with the interior of the cylindrical chamber defined by the wall 30 and is disposed near the bottom of the main body portion of the receptacle 28. A second inlet port 46 is located above port 44 and is used to inject a test sample of an agent, lewisite in the instant system, into the sampler for calibration purposes. An outlet port 48 for the contaminated liquid sample, to be discussed below, is located at the bottom center of the base plate 34, the latter sealing the bottom of the receptacle 28 and having an inverted conical configuration presenting approximately a 20 degree slope from the wall 30 to outlet port 48.

Figure 4:
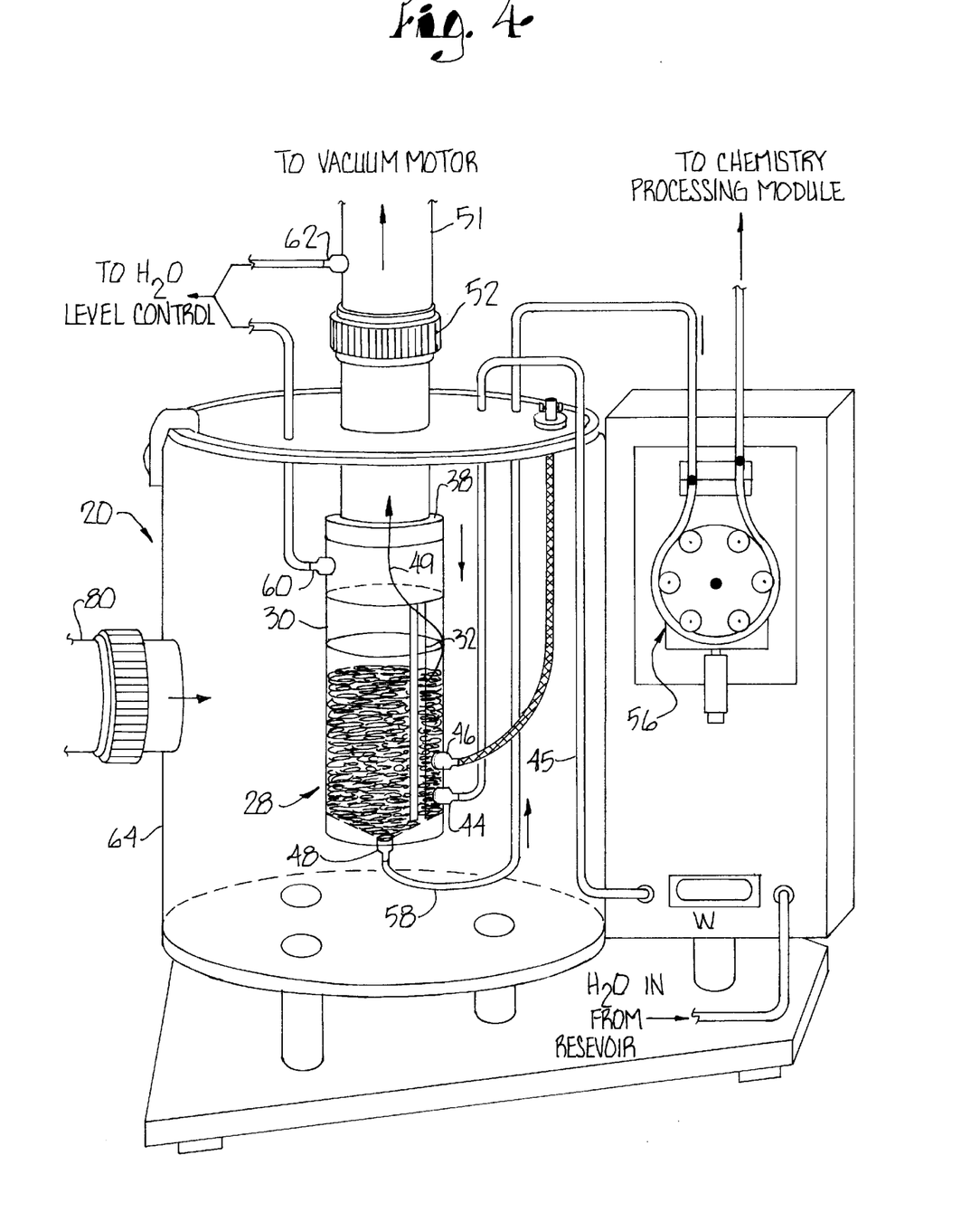
FIG. 4 is a diagrammatic, perspective view of the gas sampling unit (in operation) and associated components, including a peristaltic pump for continuously withdrawing a contaminated liquid sample from the unit.

The top of the concentrator unit is connected to a vacuum motor 50 (FIG. 5) via an intake conduit 51 secured to the receptacle 28 by any suitable means such as the PVC pipe union 52 illustrated in FIG. 2. The vacuum motor 50 is capable of drawing at least 1500 L/min of air at approximately 40 inches of $H_2O$ pressure drop across slit 32. Gas under observation, either stack gas or ambient air, is drawn in through the slit 32 and spins or swirls inside the unit in a cyclonic fashion as illustrated by the arrow 54 in FIG. 3. A controlled flow of purified water, approximately 1.5 mL/min, is added to the unit during operation via inlet port 44. The water also spins with the injected gas in a cyclonic fashion in the manner illustrated in FIGS. 3 and 4, adhering to the inside surface of the cylindrical wall 30. High turbulence occurs at the slit 32 where the incoming gas and water make contact. This turbulence results in effective scrubbing of contaminants from the gas into the water. Scrubbed gas spirals upwardly as illustrated in FIG. 4 by arrow 49 and is exhausted out the top of the unit through conduit 51. The water, however, remains within the receptacle 28 and becomes increasingly more concentrated with the contaminants.

The contaminated water sample is continuously removed by a peristaltic pump 56 (FIGS. 1 and 4) connected to outlet port 48 via line 58 and processed through the chemistry module 22 for analysis by ion chromatography. Fresh, purified scrubbing water is automatically added to the unit as the contaminated sample is removed, thus maintaining a constant water volume inside the receptacle 28 of about 7 mL. Pressure is sensed at a port 60 adjacent the upper end 38 of the receptacle 28 and at a port 62 in conduit 51, additional water from a reservoir 63 (FIG. 1) being supplied by a level control pump (not shown) via a line 45 in response to an increase in the pressure from port 60 to port 62. Such an increase in pressure is indicative of a corresponding decrease in the volume of water in receptacle 28 due to the higher resistance to the flow of gas through the receptacle 28 and conduit 51. An indicator lamp W on the housing of pump 56 is illuminated when water is flowing in line 45 from the reservoir 63 to inlet port 44.

Figure 5:
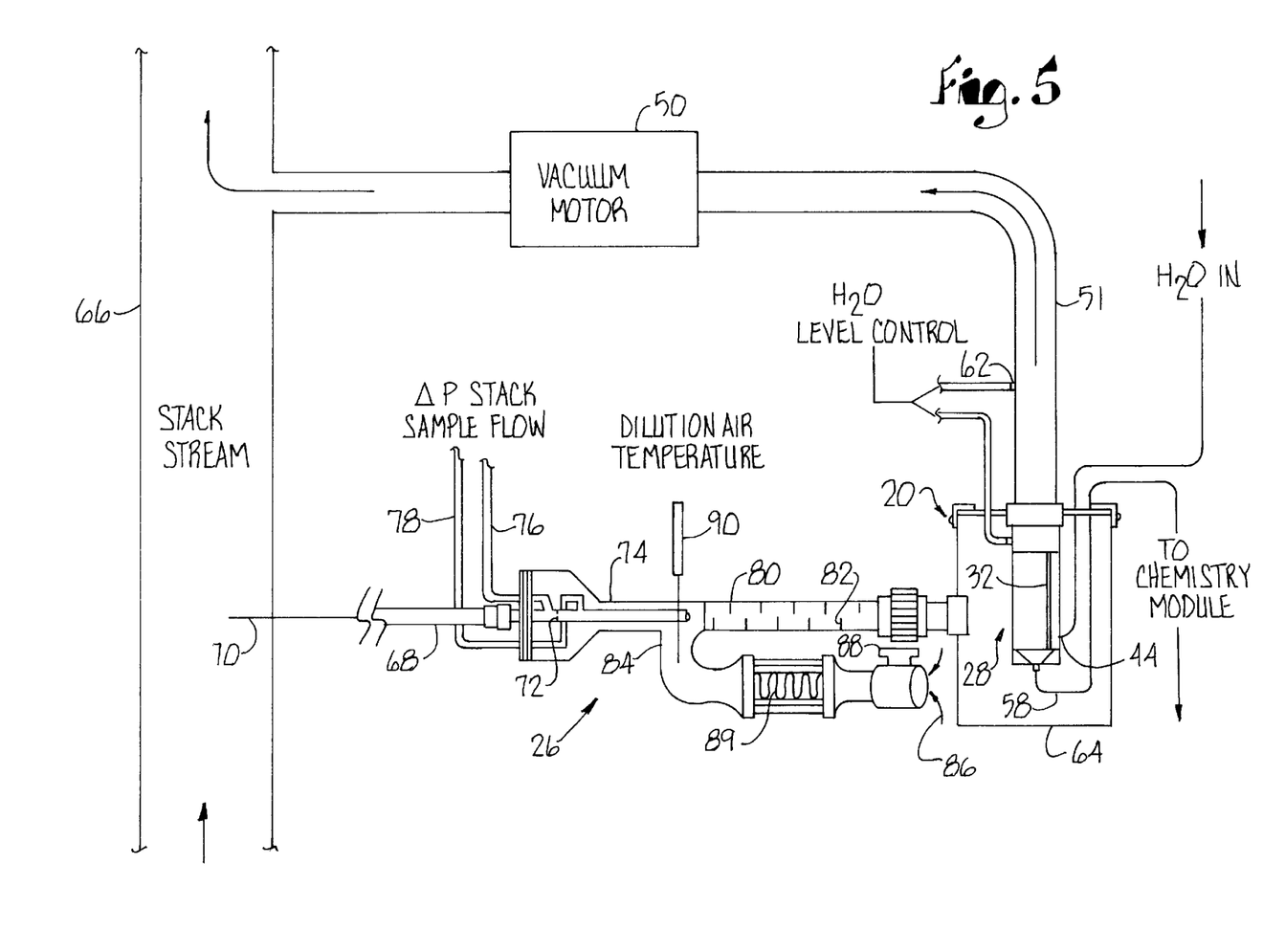
FIG. 5 is a diagrammatic view of a gas conditioner for providing the stack gas with a prescribed temperature and moisture content prior to introduction to the sampler.

For lewisite stack gas monitoring, the entire receptacle 28 is mounted inside a sealed, clear plastic chamber 64 (FIGS. 4 and 5). The chamber 64 is interfaced to an incinerator stack 66 by a heated Teflon line 68 leading from a stack gas probe 70 to the conditioner assembly 26. The stack gas conditioner allows 100 L/min of stack gas at 200° F. to be mixed and diluted with 900 L/min of ambient air for a total sampling rate of 1000 L/min. In addition to an elevated temperature, stack gas usually has a high moisture percentage, e.g. 40%. This dilution process cools the gas to about 100° F. and reduces the moisture content to approximately 4% which prevents condensation. The conditioner 26 thus allows operation of the sampler 20 at near the ambient conditions while continuously scrubbing a high volume of stack gas. Stack gas sampling rates up to 300 L/min may be obtained with this apparatus without the appearance of condensate in transfer lines or the chamber 64 surrounding the receptacle 28.

More particularly, the stack gas from line 68 passes through an orifice 72 in a pipe 74 to which line 68 is connected. The pressure on each side of the orifice 72 may be monitored via lines 76 and 78 (comprising components of a flow meter) communicating with pipe 74 on the upstream and downstream sides of orifice 72 respectively. The pipe 74 is concentrically disposed within a larger, elongated conduit 80 having baffle plates 82 spaced longitudinally therein to provide a static mixer for the incoming stack gas and ambient air which communicates with conduit 80 at a tee 84. Ambient air, represented by arrows 86, enters at a control valve 88 and passes through an internal electric heater 89 where its temperature is increased, if necessary, prior to converging with the stack gas at tee 84 and flowing through the mixer section 80 to the chamber 64 of the sampler 20. A thermometer instrument 90 at the tee 84 monitors the temperature of the dilution air.

When the contaminants are scrubbed from the stack gas into the spinning water in receptacle 28 of the sampler 20, lewisite is rapidly and quantitatively hydrolyzed to 2-chlorovinylarsonous acid (CVAA) and HCl. The CVAA solution is continuously pumped from the unit at a rate of 1 mL/min by pump 56, through a degassing filter 91 (FIG. 1), and into the chemistry processing module 22 which converts the CVAA into arsenate ions. Arsenate ion content is then measured by ion chromatography (IC) as will be discussed. Conversion of CVAA into the arsenate analyte occurs pursuant to the following reactions:

The in-line, flowing chemistry occurring in the processing module 22 (FIG. 1) utilizes potassium permanganate in an oxidation reaction as shown above, implemented by four reciprocating, high-pressure, low volume metering pumps (Eldex) 92, 93, 94 and 95. As the CVAA is pumped by pump 92 into the chemistry processing module 22, a 0.5 mL/min metered flow (pump 92) of 1 mM potassium permanganate solution ($KMnO_4$) is mixed with the 1 mL/min sample stream at a mixing tee to oxidize the CVAA into arsenate and acetylene. This process takes place in a heated reaction line represented by reactor 96 at a temperature on the order of 90° C. for a sufficient time (about seven minutes) to allow complete oxidation. Acidified hydrogen peroxide ($H_2O_2$) from pump 94 at 0.7 mL/min is then mixed with the arsenate sample stream and the admixture heated to reduce any excess potassium permanganate. The $H_2O_2$ is acidified to 4.4 mM with hydrofluoric acid (pH~3) to maintain the manganese ions in solution. The pH at this point is important in order to prevent formation of any $MnO_2$ which is insoluble and would foul the system during continuous operation.

A metered flow (pump 95) of 3.1 mM tris (hydroxymethyl) aminomethane buffer is next mixed with the sample stream to raise the pH and buffer the flowing stream. The tris buffer ionizes the arsenate to a sufficient degree that it will be effectively trapped on the anionic concentrator column of a conventional ion chromatograph. This tris buffer solution itself is a cationic buffer at pH~7 and thus does not compete for active sites on the anionic trap. The processed sample stream is finally passed through an in-line filter to remove trace precipitate before entering the ion chromatograph analysis system 24.

The chemistry processing module 22 and stack gas sampler 20 may be operated unattended for periods up to 12 hours without fouling or requiring adjustments. Preventative maintenance after 12 hours, such as filter changes and refill of reagent reservoirs, allows the sample processing system to operate 24 hours a day during demilitarization incineration tasks.

The processed sample stream from the chemistry module 22 continuously passes into the ion chromatograph 97 (such as a Dionex DX-100) of the IC system 24 for analysis. In the ion chromatograph 97, an injection valve 99 directs the processed sample into an anion concentrator tube 101. Here the arsenate ions are concentrated for a period of six minutes while the residual sample stream flows to waste at 98. At the end of this concentration period, the injection valve 99 switches, an eluant solution ($NaHCO_3/Na_2Co_3$, pH~9) is pumped through the concentrator tube by a delivery system 100, and the arsenate ions are flushed off the concentrator onto a separator column 102 for IC analysis. A guard column 104, immediately in front of the separator column 102, protects the separator from fouling by minute amounts of $MnO_2$ which are formed at the pH 9 conditions produced by the eluant solution.

Arsenate in the sample stream is chromatographed in about four minutes. An integrator 106 and associated software identifies the peak and determines the corresponding lewisite concentration and whether an alarm condition exists. The lewisite concentration and an alarm indication, if warranted, may be automatically sent to a central control room (not shown) monitoring the incineration process. The near real-time monitor may be configured to shut down plant operations when a specified emissions alarm level is exceeded.

The cycle time of the combined monitoring system is approximately 20 minutes. This cycle time includes stack gas collection, chemistry module processing for conversion of lewisite to arsenate ions, concentration of arsenate ions with the anion trap, chromatographic analysis of the collected arsenate, and finally, a determination of the corresponding lewisite emissions level and possible alarm condition.

Ambient Air Monitor

Stack gas contaminated with lewisite oftentimes also contains quantities of arsenic as combustion products. Therefore, the lewisite monitor described above is particularly useful in such stack gas monitoring applications as any lewisite present in the gas is converted to arsenate ions in the chemistry processing module 22. However, in applications in which lewisite levels in ambient air (such as in the workplace) are to be monitored, full conversion of the lewisite to the arsenate analyte may not be necessary or desired.

In such applications a modified form of the monitoring system of FIGS. 1–4 may be employed which converts lewisite present in ambient air to CVAOA in accordance with the following reactions:

This conversion to the CVAOA analyte is accomplished in a simplified system using the gas sampler 20 shown in FIGS. 1–4 and the ion chromatograph analysis system 24 of FIG. 1, without the intermediate chemistry processing module 22.

Referring to FIG. 4, in the simplified ambient air monitoring system the conduit 80 directs ambient air into the chamber 64 where the action of the vacuum motor 50 draws the ambient air into the receptacle 28 through the tangential inlet slit 32 where it intimately contacts the scrubbing liquid introduced at inlet port 44. Any lewisite contaminant is scrubbed from the air into the water by the cyclone action discussed above and illustrated in FIG. 3. The reservoir 63 supplying the receptacle 28 with water has 30% hydrogen peroxide modifier added at 5 mL per liter of water. This provides continuous, in-line oxidation of the lewisite to CVAOA within the receptacle 28. A metered flow of sample stream at, for example, a rate of 1 mL per minute is drawn from the receptacle 28 by the peristaltic pump 56, filtered, and then delivered directly to the injection valve 99 of the ion chromatograph 97.

Analysis of the CVAOA analyte proceeds in the chromatograph 97 by using a 100 microliter to 500 microliter sample loop which is automatically injected at timed intervals (approximately 5 minutes). The integrator 106 identifies the CVAOA peak and determines the corresponding lewisite concentration associated with the peak. Accordingly, the system is essentially a real-time monitor as an indication of lewisite concentration is obtained in about five minutes. It may be appreciated that this high speed of detection is particularly important in applications in which the monitor is sampling ambient air in a workplace environment.

Metals Monitor

Figure 6:
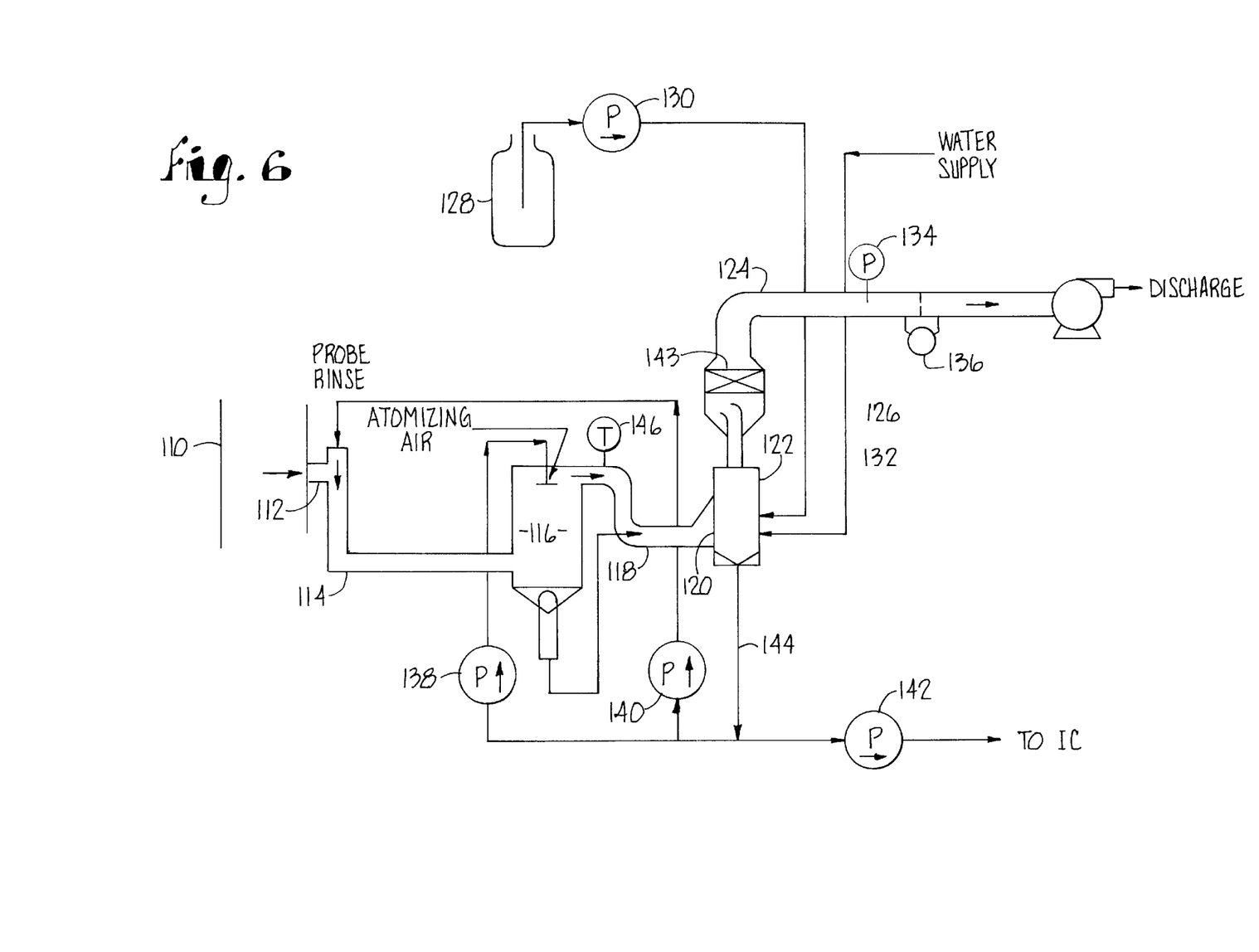
FIG. 6 is a schematic diagram of a monitoring system for use in the detection of chromium(VI) in stack gas.

FIG. 6 illustrates another application of the continuous emission monitoring system of the present invention. A stack 110 may contain toxic industrial emissions and is monitored for the presence therein of chromium(VI). A sample of the stack gas is continuously withdrawn by a probe 112 and flows via conduit 114 to a saturation tower 116. A conduit 118 leads from the outlet of tower 116 to the gas inlet slit 120 of a sampling unit of the type described above and illustrated in FIGS. 2–4. The unit in FIG. 6 has a cylindrical receptacle 122 communicating with an intake conduit 124 of a vacuum motor 126, such components corresponding to the inlet slit 32, receptacle 28, conduit 51, and vacuum motor 50 of the above-described lewisite monitor.

Purified water is supplied to the receptacle 122 via line 126 and is delivered to an inlet port corresponding to port 44 in FIGS. 2 and 4. Additionally, a feed solution is continuously supplied from a container 128 by a peristaltic pump 130 and is added to the water in receptacle 122. A line 132 leads from the outlet of pump 130 to a second port on the receptacle 122 located, for example, near the water inlet port as illustrated by port 46 in FIGS. 2 and 4. In a system as shown in FIG. 6 for detecting chromium(VI), a basic solution is utilized in order to stabilize the +6 oxidation state of chromium and prevent reduction to chromium(III). A 1N KOH solution may, for example, be delivered from container 128 by the pump 130 at a rate of from 1 to 10 mL/min.

The scrubbing water (which mixes with the KOH modifier in the receptacle 122) is supplied separately by a line 126 and is replenished as necessary to maintain the required water level in the receptacle. As discussed hereinabove with respect to FIGS. 2 and 4, a level control pump (not shown) is activated as required in response to a decrease in water volume. A vacuum gauge communicating with conduit 124 is illustrated at 134. An orifice meter 136 indicates the gas flow rate in conduit 124.

The water in receptacle 122, contaminated with the pollutants scrubbed from the gas stream, is continuously withdrawn by three peristaltic pumps 138, 140 and 142 which have a common intake line 144 corresponding to line 58 in FIG. 4. The flow rate of the liquid stream in line 144 is approximately 100 mL/min. Each of the pumps 138 and 140 may operate at flow rates up to about 50 mL/min, whereas the pump 142 provides a flow rate of from one to two mL/min for delivery to an ion chromatograph for analysis.

In the case of a chromium(VI) detector, the stack gas is cooled and humidified to near its dew point prior to entry into the receptacle 122 of the sampling unit. Assuming an incoming gas sample from probe 112 having a temperature of 400° F., the temperature of the gas at the discharge outlet of the saturation tower 116 would be, for example, 180° F. with a moisture content of from 40 to 50%. Temperature at the tower outlet is monitored as indicated by the thermometer 146. The pump 138 supplies liquid (the contaminated, dilute KOH solution) from the receptacle 122 to a nozzle in the tower 116 which mixes the liquid with atomizing air to form droplets and effect cooling and humidification. Also, the probe 112 is rinsed with the contaminated solution from receptacle 122 by the action of pump 140, the rinsing solution then flowing with the gas in conduit 114 to the tower 116. Accordingly, the stack gas is conditioned as required for chromium(VI) monitoring, and the recirculation of the contaminated sample stream by pumps 138 and 140 increases the concentration of the contaminants to, in turn, increase the sensitivity of the monitoring system. It should be noted in this respect that only a relatively small portion of the available sample stream is withdrawn by the pump 142 and delivered to the ion chromatograph for analysis.

A mesh pad demister 148 is interposed in conduit 124 to remove excess droplets from the gas exhausted from receptacle 122. This allows the collected droplets to drain back into receptacle 122.

It should be understood that the feed solution for the system of FIG. 6 is KOH since the analyte to be recognized is chromium(VI). Therefore, in other applications in which other metal contaminants are to be detected, the feed solution would be selected in order to properly condition the sample and provide the desired analyte in the contaminated sample stream. As in the chromium(VI) monitor set forth above, the contaminated sample stream containing the analyte would be fed on a continous basis to a conventional analyzer, such as an ion chromatograph or an inductively coupled argon plasma atomic emission spectrometer (ICAP-AES) to determine the presence and quantity of the analyte.

Having thus described the invention, what is claimed as new and desired to be secured by Letters Patent is as follows:

1. A method of continuously monitoring a gas under observation for contaminants therein, said method comprising the steps of:

(a) providing a sampling device including an upright receptacle having a body presenting an upwardly extending, generally cylindrical wall presenting an inside surface, (b) providing said wall with a generally vertically extending gas inlet slit therethrough tangential to the wall and substantially coextensive with said body, (c) supplying a scrubbing liquid to said body and controlling the flow thereof to maintain the liquid at a predetermined volume within said body, (d) continuously flowing the gas under observation into the body through said gas inlet slit tangentially of said wall to cause turbulent contact of the gas and scrubbing liquid and effect cyclonic spinning of the gas and scrubbing liquid within the body and the formation of a hollow, cylindrical column of spinning liquid that adheres to said inside surface, thereby scrubbing contaminants from the gas into the liquid to provide a contaminated liquid sample, (e) flowing a sufficient amount of the gas through the body in said step (d) to provide a sampling rate enabling concentration of the contaminants in the scrubbing liquid to occur in real time, (f) exhausting the gas from the body after contact with the scrubbing liquid, (g) continuously subjecting the contaminated liquid sample to chemical processing on a real-time basis to provide a detectable substance indicative of the presence of a predetermined contaminant, including adding a modifier directly to the contaminated sample in said receptacle to effect, in real time, a conversion of the predetermined contaminant to said detectable substance inside the receptacle, and thereafter (h) continuously analyzing the processed sample on a real-time basis, by a selected analytical method, to detect said substance and determine a quantity of the predetermined contaminant.

2. The method as claimed in claim 1, wherein said scrubbing liquid is supplied at a flow rate of up to approximately 10 milliliters per minute and the gas is supplied to said receptacle at a sampling rate of approximately 1,000 liters to 3,000 liters per minute.

3. The method as claimed in claim 1, wherein said predetermined contaminant is lewisite, and wherein said modifier for real-time conversion to said detectable substance is a predetermined concentration of hydrogen peroxide in water.

4. The method as claimed in claim 1, wherein said predetermined contaminant is chromium(VI), and wherein said modifier is 1N potassium hydroxide delivered to the receptacle at a rate of up to approximately 10 milliliters per minute.

5. The method as claimed in claim 1, wherein said predetermined contaminant is chromium(VI), and wherein said modifier provides a basic sample solution to maintain the chromium in a +6 oxidation state and thereby provide said detectable substance.

6. An apparatus for continuously monitoring a stack emission, air or other gas under observation for contaminants therein, said apparatus comprising:

a sampling device including an upright receptacle having a body presenting an upwardly extending, generally cylindrical wall presenting an inside surface, said wall having a generally vertically extending gas inlet slit therein tangential to the wall and substantially coextensive with said body, means communicating with said receptacle for supplying a scrubbing liquid thereto and controlling the flow thereof to maintain the liquid at a predetermined volume within said body, vacuum supply means communicating with an upper end of said body for continuously flowing the stack emission, air or other gas under observation into the body through said gas inlet slit tangentially of said wall to cause turbulent contact of the gas and scrubbing liquid and effect cyclonic spinning of the gas and scrubbing liquid within the body and the formation of a hollow, cylindrical column of spinning liquid that adheres to said inside surface, thereby scrubbing contaminants from the gas into the liquid to provide a contaminated liquid sample and exhausting the gas from the upper end of the body, said vacuum supply means flowing a sufficient amount of the gas through the body to provide a sampling rate enabling concentration of the contaminants in the scrubbing liquid to occur in real time, means communicating with said receptacle for withdrawing the contaminated liquid sample therefrom and including a chemical processing module for subjecting the sample to preselected in-line chemical processing to provide, on a real-time basis, a detectable substance indicative of the presence of a predetermined contaminant in the contaminated liquid sample, and detector means for receiving the processed sample and analyzing the same in real time to determine the presence and quantity of the predetermined contaminant.

7. The apparatus as claimed in claim 6, wherein said liquid-supplying means supplies the scrubbing liquid at a flow rate of up to approximately ten milliliters per minute, and said vacuum supply means flows the gas into said body at a sampling rate of approximately 1,000 liters to 3,000 liters per minute.

8. An apparatus for continuously monitoring a stack emission, air or other gas under observation for contaminants therein, said apparatus comprising:

a sampling device including an upright receptacle having a body presenting an upwardly extending, generally cylindrical wall presenting an inside surface, said wall having a generally vertically extending gas inlet slit therein tangential to the wall and substantially coextensive with said body, means communicating with said receptacle for supplying a scrubbing liquid and a modifier thereto, and for controlling the flow of the liquid to maintain the liquid at a predetermined volume within said body, vacuum supply means communicating with an upper end of said body for continuously flowing the stack emission, air or other gas under observation into the body through said gas inlet slit tangentially of said wall to cause turbulent contact of the gas, scrubbing liquid and modifier and effect cyclonic spinning of the gas, scrubbing liquid and modifier within the body and the formation of a hollow, cylindrical column of spinning liquid that adheres to said inside surface, thereby scrubbing contaminants from the gas into the liquid to provide a contaminated liquid sample and exhausting the gas from the upper end of the body, said vacuum supply means flowing a sufficient amount of the gas through the body to provide a sampling rate enabling concentration of the contaminants in the scrubbing liquid to occur in real time, said modifier conditioning the contaminated liquid sample to provide, on a real-time basis, a detectable substance indicative of the presence of a predetermined contaminant in the contaminated liquid sample, and detector means for receiving the conditioned sample and analyzing the same in real time to determine the presence and quantity of the predetermined contaminant.

9. The apparatus as claimed in claim 8, wherein said liquid-supplying means supplies the scrubbing liquid at a flow rate of up to approximately ten milliliters per minute, and said vacuum supply means flows the gas into said body at a sampling rate of approximately 1,000 liters to 3,000 liters per minute.

10. An apparatus for continuously monitoring a stack gas under observation for contaminants therein, said apparatus comprising:

a gas conditioner having an inlet line for receiving stack gas under observation, and means for mixing cooler air with the received gas to dilute the same and provide a conditioned gas of preselected temperature and moisture content at a rate of at least approximately 1,000 liters per minute, a sampling device including an upright receptacle having a body presenting an upwardly extending, generally cylindrical wall presenting an inside surface, said wall having a generally vertically extending gas inlet slit therein tangential to the wall, substantially coextensive with said body, and communicating with said conditioner, means communicating with said receptacle for supplying a scrubbing liquid thereto at a flow rate of up to approximately ten milliliters per minute, and controlling the flow rate to maintain the liquid at a predetermined volume within said body, vacuum supply means communicating with an upper end of said body for continuously flowing the conditioned gas into the body through said gas inlet slit tangentially of said wall to cause turbulent contact of the gas and scrubbing liquid and effect cyclonic spinning of the gas and scrubbing liquid within the body and the formation of a hollow, cylindrical column of spinning liquid that adheres to said inside surface, thereby scrubbing contaminants from the gas into the liquid to provide a contaminated liquid sample and exhausting the gas from the upper end of the body, said vacuum supply means flowing the conditioned gas through the body at a sampling rate of at least approximately 1,000 liters per minute to cause concentration of the contaminants in the scrubbing liquid to occur in real time, means connected to a liquid outlet on said receptacle for withdrawing a stream of the contaminated sample therefrom, a chemical processing module having an inlet for receiving the sample stream from said withdrawing means, and including means for converting said sample, on a real-time basis, to an analyte in detectable form indicative of the presence of a predetermined contaminant, and means for delivering a processed sample stream containing said analyte at an output of said module, and ion chromatograph means for analyzing the processed sample stream from the module output to detect said analyte and determining the quantity thereof in real time.

11. The apparatus as claimed in claim 10, wherein said converting means in the chemical processing module includes means for adding oxidizing and ionizing agents to the sample stream to convert a lewisite contaminant to an arsenate analyte for detection by said ion chromatograph means.

12. A method of continuously monitoring a gas under observation for contaminants therein, said method comprising the steps of:

(a) providing a sampling device including an upright receptacle having a body presenting an upwardly extending, generally cylindrical wall presenting an inside surface, (b) providing said wall with a generally vertically extending gas inlet slit therethrough tangential to the wall and substantially coextensive with said body, (c) supplying a scrubbing liquid to said body and controlling the flow thereof to maintain the liquid at a predetermined volume within said body, (d) continuously flowing the gas under observation into the body through said gas inlet slit tangentially of said wall to cause turbulent contact of the gas and scrubbing liquid and effect cyclonic spinning of the gas and scrubbing liquid within the body and the formation of a hollow, cylindrical column of spinning liquid that adheres to said inside surface, thereby scrubbing contaminants from the gas into the liquid to provide a contaminated liquid sample, (e) flowing a sufficient amount of the gas through the body in said step (d) to provide a sampling rate enabling concentration of the contaminants in the scrubbing liquid to occur in real time, (f) exhausting the gas from the body after contact with the scrubbing liquid, (g) continuously subjecting the contaminated liquid sample to chemical processing on a real-time basis to provide a detectable substance indicative of the presence of a predetermined contaminant, including withdrawing the contaminated sample from the receptacle and thereafter adding a modifier to the sample to effect, in real time, a conversion of the contaminant to said detectable substance, and (h) continuously analyzing the processed sample on a real-time basis, by a selected analytical method, to detect said substance and determine a quantity of the predetermined contaminant.

13. The method as claimed in claim 12, wherein said predetermined contaminant is lewisite and said scrubbing liquid is water, and wherein said modifier is an oxidant.

14. The method as claimed in claim 12, wherein said predetermined contaminant is lewisite and said scrubbing liquid is water, and wherein said modifier includes potassium permanganate, acidified hydrogen peroxide and tris (hydroxymethyl)-aminomethane buffer.

15. The method as claimed in claim 12, wherein said scrubbing liquid is supplied at a flow rate of up to approximately 10 milliliters per minute and the gas is supplied to said receptacle at a sampling rate of approximately 1,000 liters to 3,000 liters per minute.

* * * * *